United States Patent [19]
Bloomberg

[11] Patent Number: 5,433,714
[45] Date of Patent: Jul. 18, 1995

[54] TOPICAL ANESTHESIA METHOD FOR EYE SURGERY, AND APPLICATOR THEREFOR

[76] Inventor: Leroy Bloomberg, 1651 W. Main St., Newark, Ohio 43055

[21] Appl. No.: 53,593

[22] Filed: Apr. 27, 1993

Related U.S. Application Data

[63] Continuation-in-part of Ser. No. 45,262, Apr. 6, 1993, abandoned.

[51] Int. Cl.⁶ .......................................... A61M 35/00
[52] U.S. Cl. ............................... 604/289; 604/290; 604/294; 623/4; 128/898
[58] Field of Search ............... 604/19, 49, 289–290, 604/294, 303, 304; 602/41–51, 74; 128/897–898; 623/4

[56] References Cited

U.S. PATENT DOCUMENTS

| | | | |
|---|---|---|---|
| 3,995,635 | 12/1976 | Higuchi et al. | 604/294 |
| 4,540,408 | 9/1985 | Lloyd | 604/289 |
| 5,171,307 | 12/1992 | Sanning | 604/289 |

FOREIGN PATENT DOCUMENTS 1544385  2/1990  U.S.S.R. .............................. 128/898

OTHER PUBLICATIONS

Paul S. Koch, "Delighted with results of his RK, surgeon schooled in pain, glare", Ocular Surgery News, 10: No. 14, Jul. 15, 1992.

Robert E. Fenzl, "Indications for use of topical anesthesia in cataract surgery", Ocular Surgery News, 10: No. 13, Jul. 1, 1992.

Primary Examiner—Randall L. Green
Assistant Examiner—P. Zuttarelli
Attorney, Agent, or Firm—Hoffmann & Baron

[57] ABSTRACT

An applicator is disclosed for use in anesthetizing the eye prior to surgery, such as anterior segment surgery. The applicator includes an annular wall which defines an opening sufficiently large to expose the cornea of an eye. The applicator is made from a porous, absorbent material capable of absorbing a topical anesthetic. A method for using such an applicator is also provided. The method includes the steps of positioning the applicator upon the eye such that the wall substantially conforms to the surface configuration of the eye while substantially entirely exposing the cornea portion of the eye through the opening.

20 Claims, 2 Drawing Sheets

TOPICAL ANESTHESIA METHOD FOR EYE SURGERY, AND APPLICATOR THEREFOR

CROSS REFERENCE TO RELATED APPLICATION

This application is a continuation-in-part of application Ser. No. 08/045,262 filed Apr. 6, 1993, now abandoned.

BACKGROUND OF THE INVENTION

1. Field of the Invention

The field of the invention relates to topical anesthesia techniques, and applicators for providing anesthetic agents to the eye.

2. Brief Description of the Prior Art

For many years it has been traditional to use retrobulbar anesthesia when performing eye surgery. This technique has been described as early as 1884. While complications of retrobulbar anesthesia are few, they can be quite serious. These complications include: retrobulbar hemorrhage, respiratory depression, intradural or subarachnoid injection, optic nerve damage and perforation of the eye. In the early 1980's, in hopes of eliminating serious complications, many surgeons began to use periocular anesthesia with hopes that this technique would be a much safer one. In 1992, a number of eye surgeons in the United States began using topical anesthesia (no injections around the eye) for cataract surgery, which now totally eliminates the complications of the needle.

Retrobulbar anesthesia depends on a small volume (2-4 cc) of anesthesia being injected into the muscle cone directly behind the eye. In order to do this, a long needle ($1\frac{1}{4}"-1\frac{1}{2}"$) is used. The patient is typically advised to look superior nasally while the needle is placed along the outer third of the lower lid. Once the needle penetrates the skin for about 1 cm, the needle is directed upward and nasal into the muscle cone. This also places the needle close to the posterior portion of the eye and near the optic nerve. Two to four cubic centimeters of anesthetic are injected at this point. Because the needle is directed upward and inward, there is a chance, especially in long myopic eyes, that the needle could penetrate the globe.

Another possible serious complication is optic nerve damage. Optic nerve damage can occur if too much anesthetic is injected in the retrobulbar space causing compression of the optic nerve. This could also occur if the needle penetrates the optic nerve sheath allowing the anesthetic to be injected directly along the optic nerve sheath. The latter would cause direct compression of the optic nerve. Another mechanism of optic nerve damage could occur if the needle is placed directly into the optic nerve. Compression of the optic nerve could result in central retinal vein occlusion, and either of these complications could result in optic atrophy and total blindness. Injecting anesthetic into the optic nerve sheath could allow the anesthetic to enter the subarachnoid or subdural space, resulting in respiratory depression and even transient contralateral blindness as well as mid-brain anesthesia. In order to avoid many of these complications, it has been suggested that a dull needle be used, but this has still not eliminated the problem.

Periocular anesthesia has been employed in the hope of eliminating some of the potentially serious complications of retrobulbar anesthesia. One periocular anesthesia technique utilizes a shorter, 26 gauge needle having a length of $\frac{3}{4}"-1"$. The needle is deliberately directed away from the eye and the anesthetic is deliberately injected outside the muscle cone. In order for this technique to be successful, a much larger volume of anesthetic (8-10 cc) is required. Because the anesthetic must disperse around the orbit, the surgeon must allow 12-20 minutes for it to take effect.

Even though periocular anesthesia is safer than retrobulbar anesthesia, and even though it has been documented that this technique reduces the incidence of complications, they can still occur if the needle is inadvertently placed in the wrong direction. Though complications with periocular anesthesia are rare, they can be serious and can even result in total loss of vision or loss of the eye.

By using topical anesthesia, any risk associated with the needle is eliminated. Topical anesthesia is an effective and reliable method of obtaining ocular anesthesia and gives the patient the benefits of increased safety, rapid return of vision with no loss of ocular motility and little risk of ptosis or double-vision. The anesthetic agents, e.g. tetracaine or Xylocaine, are typically applied to the eye as drops and/or with a sponge which has been soaked with the selected agent.

A ring-shaped structure having an inner diameter of 12 mm and an external diameter of 17.5 mm has also been available as an applicator for anesthetic agents. This applicator is made from polyvinyl alcohol, and includes a wick extension extending from the ring-shaped body. It has not gained wide acceptance in the field of ophthalmic surgery, however, and has a potentially serious drawback in that the inner diameter of the ring-shaped body is not sufficiently large to keep the topical anesthetic agents away from the limbus. The anesthetic is in direct contact with the corneal epithelium when the applicator is used, which can result in toxic effects. The extension may also allow the anesthetic to drain off from the area requiring anesthetization.

SUMMARY OF THE INVENTION

It is an object of the invention to provide an applicator for anesthetizing the eye which prevents an overdose of an anesthetic agent while permitting irrigation of the cornea when the eye is held open.

It is another object of the invention to provide a method of applying a topical anesthetic agent to the eye using such an applicator.

In accordance with these and other objects of the invention, an applicator is provided which includes a porous, absorbent, body having an at least generally annular wall defining an opening large enough to substantially entirely expose the cornea. The opening preferably has a diameter at least thirteen millimeters. The body preferably has a ring-shaped configuration, the outer diameter of which is between about three and six millimeters larger than the diameter of the opening.

A method in accordance with the invention includes the steps of providing an applicator having a generally annular wall, causing the applicator to absorb a topical anesthetic agent, and placing the applicator upon the eye such that the entire cornea, including the limbus, is exposed through the opening. A further step may include irrigating the cornea through the opening. The applicator may be removed immediately prior to making a surgical incision. It may also be applied intraoperatively to enhance anesthesia if necessary.

DETAILED DESCRIPTION OF THE INVENTION

Figure 1:
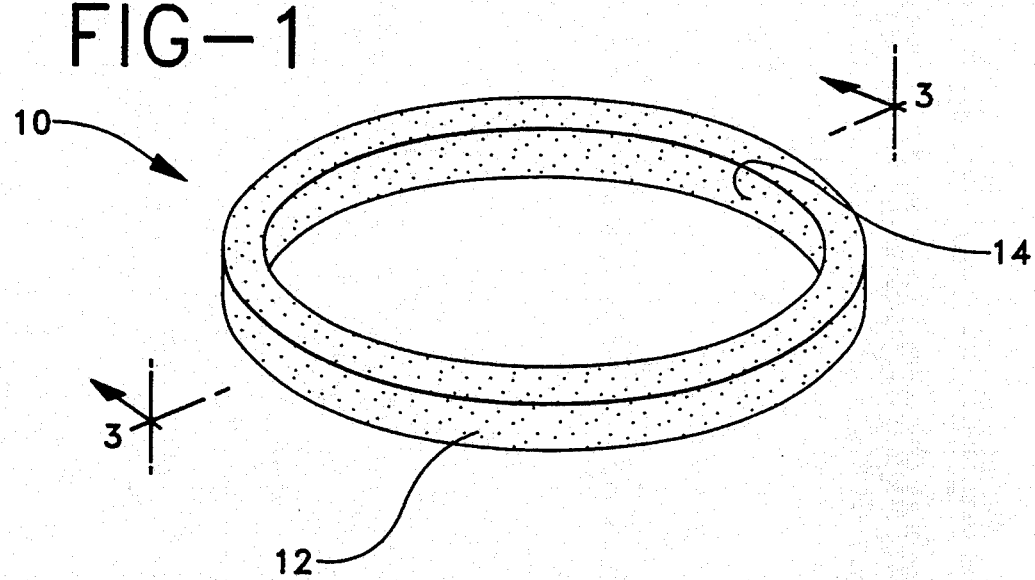
FIG. 1 is a greatly enlarged top perspective view of an applicator according to the invention.
Figure 2:
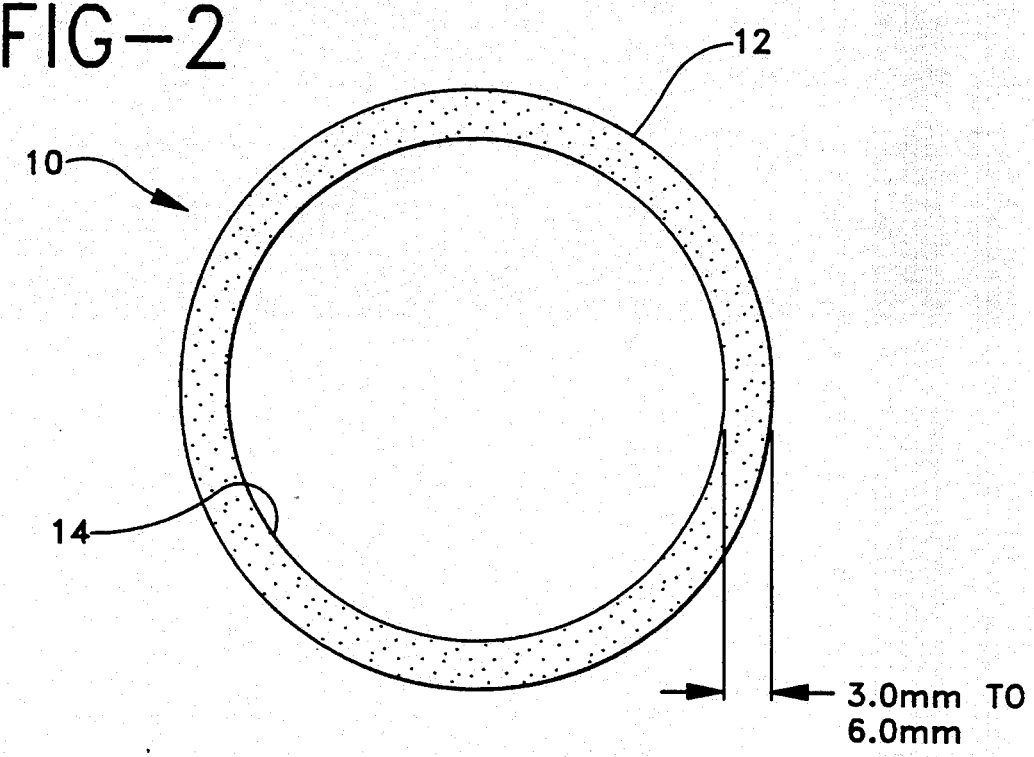
FIG. 2 is a top plan view thereof.
Figure 3:
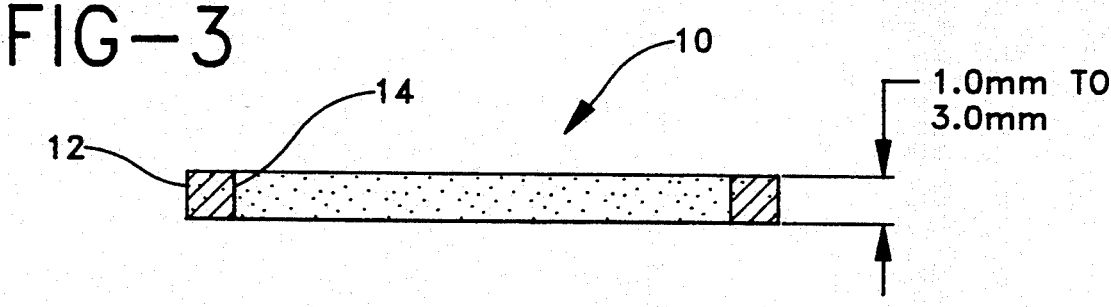
FIG. 3 is a sectional view thereof taken through line 3-3 of FIG. 1.

An applicator 10 is disclosed which is specifically designed for applying anesthetic to the eye. The applicator according to the preferred embodiment of the invention has a substantially ring-shaped body 12, as shown in FIGS. 1-3. A circular opening 14 extends through the body. The opening 14 has a diameter of at least about thirteen millimeters, and is preferably slightly larger than the diameter of the limbus of an adult human eye. The limbus is the small, circular transition zone between the cornea and the sclera.

The outside diameter of the applicator body wall bounding the opening is about three to six millimeters larger than the inside diameter thereof. Preferably, the outside diameter is about four millimeters wider. The preferred applicator in accordance with the invention accordingly has an outside diameter of about eighteen millimeters and an inside diameter of about fourteen millimeters.

The applicator is made from a porous, absorbent material such as polyvinyl alcohol, that can be sterilized. A lint-free instrument wipe, such as that sold under the trademark MENTOR by Mentor O & O Inc., may be successfully employed for fabricating the applicator. The body 12 preferably has a thickness of between about one and three millimeters. The thickness is preferably uniform. The body is gas-sterilized and stored within a sterile package (not shown) prior to use.

A technique for successfully employing the applicator according to the invention shall now be described in connection with a patient who is to undergo cataract surgery. It will be understood that the applicator may be used to provide anesthetics to the eye prior to and during other types of eye surgery as well.

The patient is instructed to begin using VOLTAREN 0.1% eye drops at a rate of one drop every four hours the day before surgery. (VOLTAREN is a trademark of Ciba-Geigy Corporation). On the morning of surgery, one drop is applied every fifteen minutes for a period of one hour.

In the pre-operative area, one drop of proparacaine 0.5% is instilled. Approximately 30 seconds later, one drop of betoxalol 0.5% is instilled. Three to five minutes later, one drop of phenylephrine 2.5%, one drop of cyclopentolate 1%, and one drop of VOLTAREN 0.1% are instilled. An external prep is done using a povidoneiodine swab to clean the lids. One drop each of phenylephrine 2.5%, cyclopentolate 1%, and VOLTAREN 0.1% are instilled five minutes apart until the pupil is fully dilated. The eye is irrigated with four to five drops of lidocaine 4% and two drops of povidone-iodine, one half strength. After five minutes the lidocaine 4% is repeated. The patient then is transferred to the operating room. A third instillation of lidocaine 4% is provided prior to the prep in the operating room.

Figure 4:
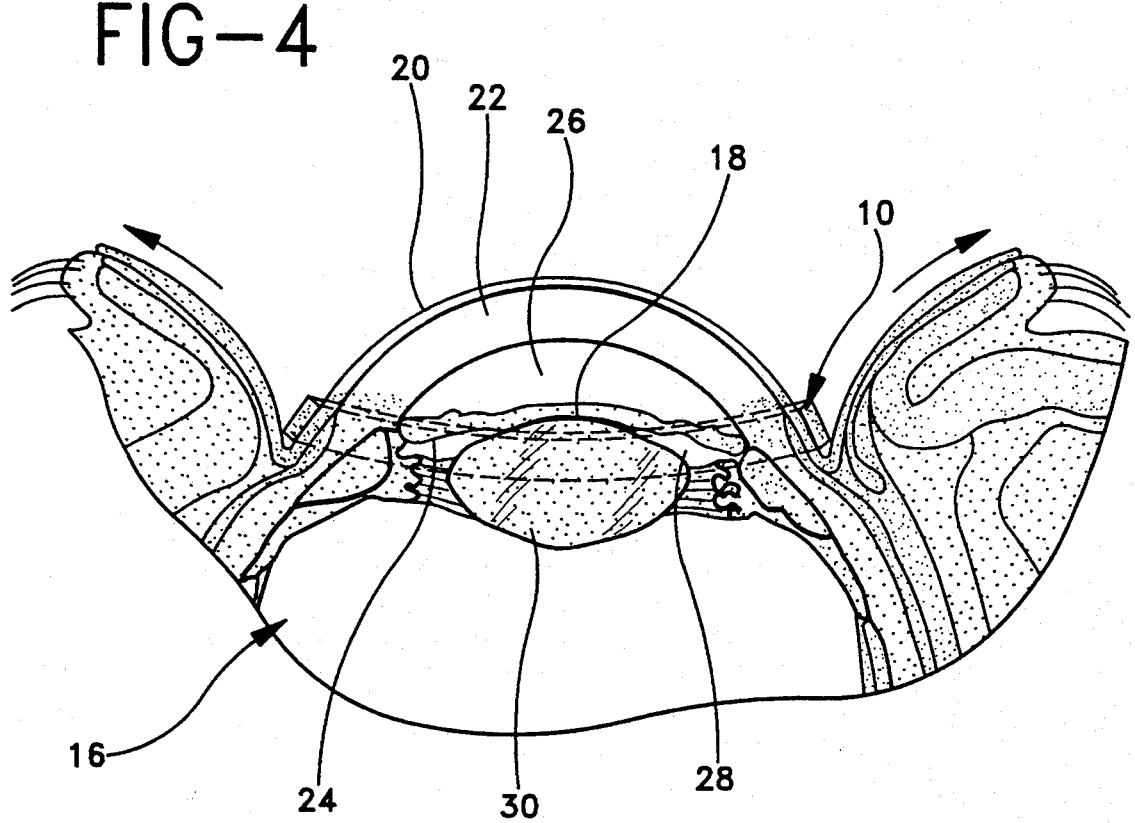
FIG. 4 is a sectional view of the applicator applied to an eye.
Figure 5:
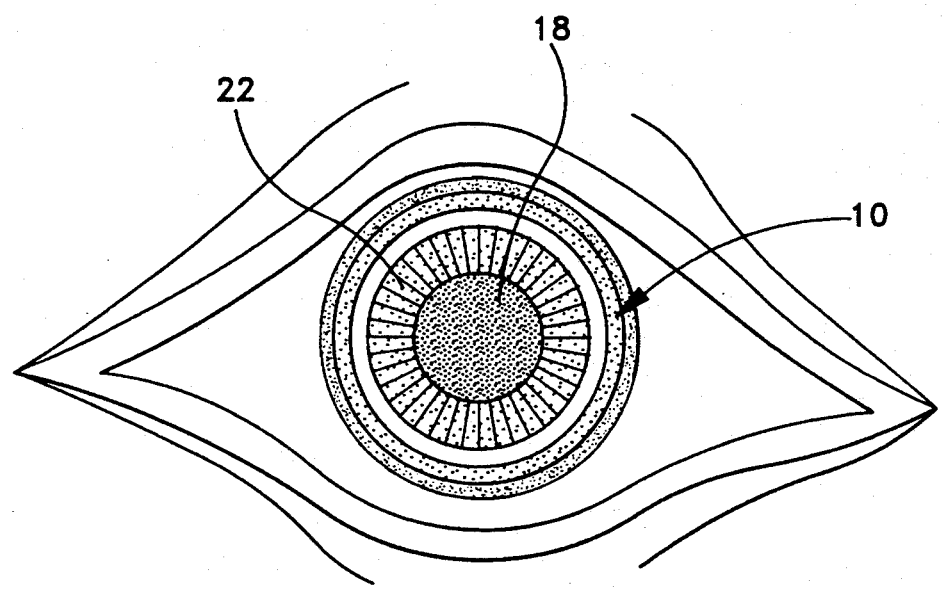
FIG. 5 is a top plan view of the applicator applied to an eye.

Intraoperatively, the patient is prepped and draped in the manner usual for eye surgery. The eyelids are held back by a speculum (not shown) so that the globe is widely exposed. The applicator 10 is soaked in topical anesthetic (e.g. tetracaine 0.5%, 2% or 4%; lidocaine 0.25%, 0.5%, or 0.75%, or 0.75% marcaine or carbocaine) and is placed on the eye 16 as shown in FIGS. 4 and 5. The applicator, as wetted, is sufficiently flexible to conform to the surface configuration of the eye, and rests upon the conjunctiva just around the limbus of the eye. The applicator preferably never contacts the cornea. It remains on the eye, thereby maintaining a proper level of the topical anesthesia until the surgeon is ready to begin the procedure. The cornea, being smaller in diameter than the opening 14, remains totally uncovered. The applicator is ordinarily removed prior to making an incision.

Sedation and monitored care are preferably used along with topical anesthesia and verbal reassurance for cataract surgery. The anesthetist may inject small doses of fentanyl (SUBLIMAZE, Janssen Pharmaceutica Inc.) 25-50 mcg or midazolam (VERSED, Roche Laboratories) 1-2 mg intravenously. The sedation, if necessary, is titrated slowly until the patient is relaxed. The patient is monitored and vital signs are recorded throughout the surgical procedure. The patient may feel some pressure, but should not experience pain during the procedure. Patients may leave the operating room without a patch.

The use of the applicator 10 as described above allows the level of the topical anesthesia to be maintained until the surgical procedure begins. It may also be used intra-operatively to enhance anesthesia. Irrigation fluid may be provided through the central opening 14 when necessary. The use of the applicator having such an opening centered with respect to the cornea helps prevent an overdose of the topical anesthetic to the epithelium 20 of the cornea 22.

Topical anesthesia is a safe and effective method of obtaining ocular anesthesia, particularly when the anesthetic agents are effectively isolated from the corneal epithelium. By using the procedure described above, many complications associated with the injection of an anesthetic, including ptosis, diplopia, optic nerve damage, retrobulbar hemorrhage, respiratory depression, intradural or subarachnoid injection or perforation of the eye, can be eliminated. Patients are very comfortable throughout the procedure, and generally experience rapid visual recovery following surgery. They are able to blink and move their eyes normally. Many are even able to read while still in the post-op area of the surgi-center.

While the applicator according to the invention is preferably a substantially ring-shaped structure having the dimensions described herein, its construction can be varied if desired. The body of the applicator may, for example, have an ovular configuration. If a circular opening is provided therein, the wall of the body would, of course, have a variable width. If a non-circular opening is employed, the minimum (i.e. smallest) diameter thereof should be at least large enough to entirely expose the cornea. The size and configuration of the wall should be such that it is easily applied to the eye and fits entirely upon the eye. The opening should have a minimum diameter which at least approximates the diameter of the limbus, and therefore exposes the cornea in its entirety. The iris 24, which separates the anterior and posterior chambers 26, 28 and controls the size of the pupil 18, as shown in FIG. 4, is also exposed by the opening within the applicator. As discussed above, the applicator is preferably removed prior to making an incision. The above technique is particularly effective when conducting surgery to remove and/or replace the lens 30.

The particular anesthetic(s) used in conjunction with the applicator may differ from those specifically discussed herein depending upon the needs of the patient and surgeon. Regardless of the anesthetic which is used, the applicator 10 is applied to the eye such that the corneal epithelium avoids contact with the applicator body 12.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of performing a surgical procedure upon the eye, comprising:
   providing a porous, absorbent body containing an effective amount of anesthetic agent and having an opening extending therethrough;
   applying said body to an eye such that the cornea and limbus of said eye are entirely exposed by said opening and an effective amount of anesthetic agent is provided to the area of the eye immediately surrounding the cornea and limbus by said body, and
   making an incision within the eye.

2. A method as described in claim 1, including the step of removing the body from the eye prior to making the incision.

3. A method as described in claim 1, including the step of irrigating the eye through the opening in the body.

4. A method as described in claim 1, wherein the body is applied to the eye such that the body substantially conforms to the surface configuration of the eye.

5. A method as described in claim 1, including the step of soaking the body in a topical anesthetic agent prior to applying the body to the eye.

6. A method as described in claim 5, wherein the body is applied to the eye such that the body substantially conforms to the surface configuration of the eye.

7. A method as described in claim 1, wherein said body has a substantially ring-shaped configuration having an outside diameter of about eighteen millimeters and wherein said body is applied to the eye such that the opening is centered with respect to the cornea.

8. A method as described in claim 6, including the steps of dilating the pupil and applying the body to the eye such that the dilated pupil is substantially fully exposed by the opening.

9. A method as described in claim 8, including the step of soaking the body in a topical anesthetic agent prior to applying the body to the eye.

10. A method of applying a topical anesthetic agent to the eye for a surgical procedure therein, comprising:
    providing a porous, absorbent body having an at least generally annular wall defining an opening extending therethrough, the dimensions of the wall being such that the wall may be positioned in its entirety upon the eye, the dimensions of the opening being such that the cornea and limbus of the eye may be entirely exposed by the opening;
    causing the body to absorb a topical anesthetic agent;
    applying the body to the eye such that the wall of the body substantially conforms to the surface configuration of the eye, the cornea and limbus are entirely exposed by the opening, and the area immediately surrounding the cornea and limbus is covered by the body, and
    allowing the body to remain upon the eye such that an effective amount of anesthetic agent is provided to the area of the eye immediately surrounding the cornea and limbus.

11. A method as described in claim 10, including the step of irrigating the eye through the opening.

12. A method as described in claim 10, wherein the wall has a substantially uniform thickness between 1–3 mm.

13. A method as described in claim 10, wherein the step of causing the body to absorb a topical anesthetic agent includes soaking the body in the topical anesthetic agent.

14. A method as described in claim 13, wherein the opening is substantially circular and is larger in diameter than the limbus of the eye, including the step of applying the body to the eye such that the cornea is centered with respect to the opening.

15. A method as described in claim 10, wherein the opening has a diameter of about 14 mm.

16. A method as described in claim 15, wherein the wall has a substantially uniform width of between about 3–6 mm.

17. A method as described in claim 15, wherein the wall has a width of about 4 mm.

18. A method of performing a surgical procedure upon the eye, comprising:
    providing a substantially ring-shaped absorbent body made from polyvinyl alcohol, said body including an opening of at least about thirteen millimeters such that the cornea and limbus of the eye can be entirely exposed upon placement of said body upon the eye;
    wetting said body with a topical anesthetic;
    applying said body to the eye such that the cornea and limbus are entirely exposed by said opening and an effective amount of anesthetic agent is provided to the area of the eye immediately surrounding the cornea and limbus, and
    making an incision within the eye.

19. A method as described in claim 18 including the step of removing said body prior to making said incision.

20. A method as described in claim 18 wherein said incision is part of a surgical procedure, including the step of leaving said body in place upon the eye during said surgical procedure.

* * * * *

UNITED STATES PATENT AND TRADEMARK OFFICE
CERTIFICATE OF CORRECTION

PATENT NO.   :   5,433,714
DATED        :   July 18, 1995
INVENTOR(S)  :   Bloomberg It is certified that error appears in the above-indentified patent and that said Letters Patent is hereby corrected as shown below:

Claim 8, col. 5, line 57, change "6" to --7--;

Claim 10, col. 6, line 2, change "therein" to --thereon--;

Signed and Sealed this

Twenty-sixth Day of March, 1996

Attest:

BRUCE LEHMAN

*Attesting Officer*                *Commissioner of Patents and Trademarks*